United States Patent [19]
Carol

[11] Patent Number: 5,411,026
[45] Date of Patent: May 2, 1995

[54] METHOD AND APPARATUS FOR LESION POSITION VERIFICATION

[75] Inventor: Mark P. Carol, Milford, N.Y.

[73] Assignee: NOMOS Corporation, Sewickley, Pa.

[21] Appl. No.: 134,168

[22] Filed: Oct. 8, 1993

[51] Int. Cl.6 .............................................. A61B 8/00
[52] U.S. Cl. .................... 128/660.03; 128/916
[58] Field of Search ............... 128/660.01, 660.03, 128/662.03, 653.1, 24 EL, 660.09, 916

[56] References Cited

U.S. PATENT DOCUMENTS

| | | | |
|---|---|---|---|
| 3,555,888 | 1/1971 | Brown | 128/916 |
| 5,060,650 | 10/1991 | Wurster et al. | 128/660.03 |
| 5,167,165 | 12/1992 | Brucher et al. | 128/662.03 |
| 5,219,401 | 6/1993 | Cathignol et al. | 128/660.03 |
| 5,285,772 | 2/1994 | Rattner | 128/660.03 |

*Primary Examiner*—George Manuel
*Attorney, Agent, or Firm*—Ben D. Tobor

[57] ABSTRACT

A method and apparatus for verifying the position of a lesion in a patient's body compares the location of the lesion in CT slices with the position of the lesion in ultrasound images taken while the patient lays on the treatment table of a linear accelerator.

20 Claims, 5 Drawing Sheets

METHOD AND APPARATUS FOR LESION POSITION VERIFICATION

BACKGROUND OF THE INVENTION

1. Field of the Invention

The invention relates to a method and apparatus for verifying the position of a lesion to be treated by a radiation therapy device operating in accordance with a radiation therapy plan.

2. Description of the Prior Art

Modern day radiation therapy of cancerous tumors, or lesions, has two goals: eradication of the tumor and avoidance of damage to healthy tissue and organs present near the tumor. It is believed that a vast majority of tumors can be eradicated completely if a sufficient radiation dose is delivered to the tumor volume; however, complications may result from use of the necessary effective radiation dose, due to damage to healthy tissue which surrounds the tumor, or to other healthy body organs located close to the tumor. The goal of conformal radiation therapy is to confine the delivered radiation dose to only the tumor volume defined by the outer surface of the tumor, while minimizing the dose of radiation to surrounding healthy tissue or adjacent healthy organs.

Conformal radiation therapy treatment typically uses a linear accelerator as a source of the radiation being used to treat the tumor. The linear accelerator typically has a radiation beam source which is rotated about the patient and directs the radiation beam toward the tumor, or lesion, to be treated. Various types of devices have been proposed to conform the shape of the radiation treatment beam to follow the spatial contour of the tumor as seen by the radiation treatment beam as it passes through the patient's body into the tumor, during rotation of the radiation beam source, which is mounted on a rotatable gantry of the linear accelerator. Multileaf collimators, which have multiple leaf, or finger, projections which can be moved individually into and out of the path of the radiation beam, can be so programmed, and are examples of such devices. Various types of radiation treatment planning systems can create a radiation treatment plan, which when implemented will deliver a specified dose of radiation shaped to conform to the lesion, or tumor, volume, while limiting the radiation dose delivered to sensitive surrounding healthy tissue or adjacent healthy organs.

A basic problem in radiation therapy is knowing where the target, or lesion or tumor, is located at the time the radiation therapy treatment is occurring. It is assumed that the patient's position and the target organ's position within the patient will be grossly the same at the time of radiation treatment, as it was at the time the radiation treatment plan was created. If the position of the target organ, or lesion or tumor, is not the same as it was at the time the treatment plan was determined, the conformal dose of radiation may not be delivered to the correct location within the patient's body. Since patients are not always positioned properly on the treatment table of the radiation therapy device, which is typically a linear accelerator, and since organs of a patient may move within the patient from day to day, the target organ, or lesion or tumor, may not be positioned at the exact location where the radiation therapy plan has assumed it would be located. Thus, present day radiation therapy plans typically regard the target organ to occupy a space in the patient's body which is larger than it really occupies, in order to insure that the target organ, or tumor or lesion, regardless of its location within the patient's body, falls within the volume of tissue which receives the desired radiation treatment dose. A disadvantage of such conventional radiation therapy plans is that there is a major concern associated with increasing the volume of tissue which is treated, to insure that the actual target organ receives the desired dose of radiation. Because some healthy tissue surrounds the target organ, or healthy organs lie adjacent to the target organ, delivering the maximum desired radiation dose to this larger volume of tissue may occur and increase risk of damaging such non-target tissue, or surrounding healthy tissue or adjacent healthy organs. This increased risk may cause oncologists to deliver a radiation dose to the larger treatment volume, which is safer for the non-target tissue, with the potential disadvantage of underdosing some portion of the target organ.

Accordingly, prior to the development of the present invention, there has been no lesion position verification system or method for verifying the position of a lesion within a body of a patient for use in a radiation treatment plan, which: regardless of the position of the patient on the treatment table, can verify that the position of the lesion to be treated conforms to the position of the lesion utilized in the radiation treatment plan; and prevents treating healthy tissue surrounding the lesion, or healthy organs located adjacent the lesion, from being exposed to an undesired level of radiation.

Therefore, the art has sought a method and apparatus for verifying the position of a lesion, within a body of a patient for use in a radiation treatment plan, which: verifies that the position of the lesion to be treated by the radiation therapy device is positioned to conform to the position of the lesion used in the radiation treatment plan; and prevents healthy tissue surrounding the lesion, or healthy organs located adjacent the lesion, from being exposed to an undesired amount of radiation.

SUMMARY OF THE INVENTION

In accordance with the invention, the foregoing advantages have been achieved through the present method for verifying the position of a lesion, having an outer surface, within a body of a patient for use in a radiation treatment plan which includes a plurality of diagnostic images, which each depict an outline of the outer surface of the lesion. The present invention includes the steps of: disposing the patient on a treatment table of a radiation therapy device; disposing on the treatment table a means for generating an ultrasound image; generating at least one two-dimensional ultrasound image of the lesion in the patient's body, with the ultrasound image generating means being disposed in a known geometric orientation for each ultrasound image generated; outlining the outer surface of the lesion in the at least one ultrasound image; and comparing the outlines of the outer surface of the lesion of the at least one ultrasound image with the outline of the outer surface of the lesion of at least one of the diagnostic images, whereby the position of the lesion with respect to the radiation therapy device may be verified to conform to a desired position of the lesion in the radiation treatment plan.

Another feature of the present invention may include the step of determining an amount of movement of the lesion required to dispose the lesion, with respect to the radiation therapy device, to conform to the desired position of the lesion in the radiation treatment plan. A further feature of the present invention may include the step of moving the lesion with respect to the radiation therapy device to dispose the lesion to conform to the desired position of the lesion in the radiation treatment plan. An additional feature of the present invention is that the step of moving the lesion may be performed by moving the treatment table with respect to the radiation therapy device, by rotating the treatment table with respect to the radiation therapy device, by rotating the gantry of the radiation treatment device and by rotating a collimator of the radiation therapy device.

Another feature of the present invention may include the steps of: forming a three-dimensional rendering of the outline of the lesion from the plurality of two-dimensional ultrasound images which have had the outer surface of the lesion outlined; and comparing the three-dimensional rendering of the outline of the lesion of the ultrasound images with a three-dimensional rendering of the outline of the lesion of the radiation treatment plan. A further feature of the present invention may include the step of disposing the patient on the treatment table by fixating the patient to the table with a patient fixation device in a known orientation.

In accordance with another aspect of the present invention, the foregoing advantages have also been achieved through a lesion position verification system for use in a radiation therapy plan for treating a lesion within a body of a patient. This aspect of the present invention includes: a means for generating at least one ultrasound image of the lesion in the patient's body; and a means for indicating the position of the means for generating the at least one ultrasound image when the ultrasound image is generated, whereby the position of the lesion in the ultrasound image can be compared with the position of the lesion in the radiation therapy plan. Another feature of this aspect of the present invention is that the means for generating the ultrasound image may be an ultrasound probe, including a means for mounting the ultrasound probe to a radiation therapy device. Another feature of the present invention is that the means for determining the position of the means for generating the at least one ultrasound image, may be a position sensing system which indicates the position of the ultrasound image generating means with respect to a radiation therapy device. An additional feature of this aspect of this present invention may include a means for comparing the position of the lesion in the at least one ultrasound image with the position of the lesion in the radiation therapy plan.

The lesion position verification system and method for verifying the position of a lesion of the present invention, have the advantages of preventing healthy tissue surrounding the lesion, or healthy organs located adjacent the lesion, from being exposed to an undesired amount of radiation; and permit the verification that the position of the lesion with respect to the radiation therapy treatment device conforms to the desired position of the lesion in the radiation treatment plan.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF THE INVENTION

Figure 1:
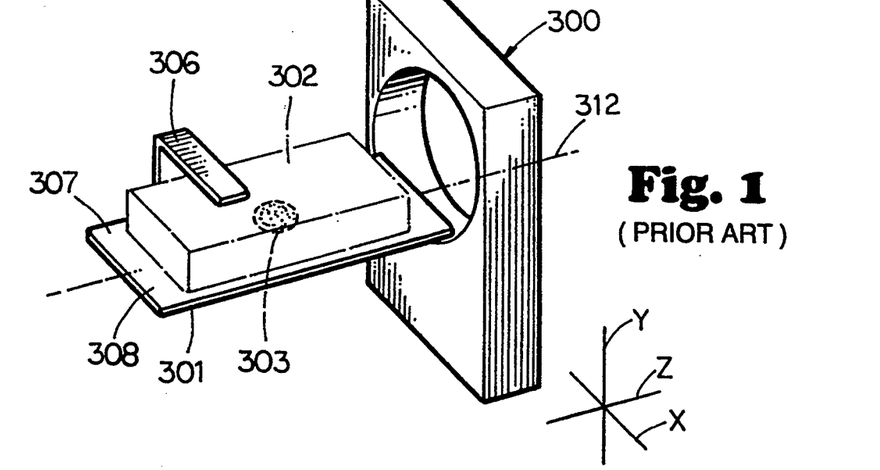
FIG. 1 is a perspective view of a conventional imaging device with a patient schematically illustrated on the imaging table, the patient having a lesion disposed within the patient's body.
Figure 2:
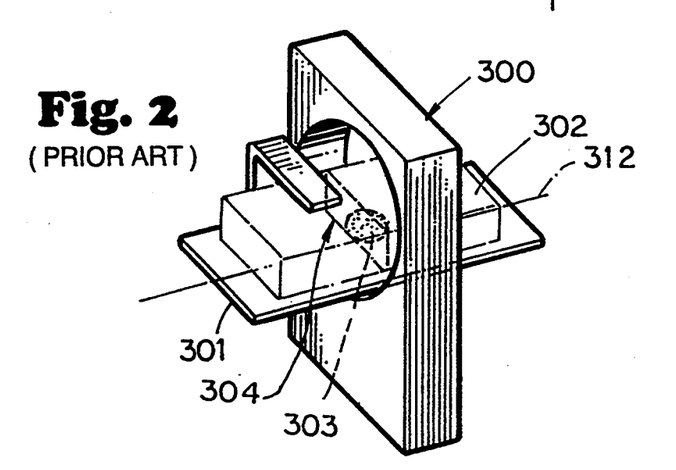
FIG. 2 is a perspective view of the imaging device of FIG. 1, with the patient passing through the imaging device.

With reference to FIG. 1, a conventional imaging device 300 is schematically shown and includes a conventional imaging table 301, upon which is disposed a patient 302 having a lesion 303 within the patient's body 302. Imaging device 300 may be a computerized tomographic ("CT") scanning device, as illustrated in FIG. 1, or may alternatively be a magnetic resonance ("MR") imaging device, as are known in the art. CT scanning devices, such as imaging device 300, produce an image representing a "slice" of body tissue 304 (shown in phantom lines in FIG. 2), one such slice being illustrated in FIG. 3. A plurality of images, or diagnostic images, 304 are obtained by the imaging device 300, and this series of "slices" which constitute a complete CT study, represent a three-dimensional picture of a particular volume, or section, of the patient's body, such as that portion of the patient's body 302 which includes lesion 303 therein. The plurality of "slices" or diagnostic images, 304 are obtained by moving the patient 302, disposed upon imaging table 301, through imaging device 300 in the direction shown by arrow 305 as illustrated in FIG. 2.

If desired, as hereinafter described in greater detail, the orientation of the patient 302 upon imaging table 301 when the slices, or images, 304 are made, may be predetermined, or known, as by fixating the patient's body 302 to the imaging table 301 by use of a conventional fixation device 306. Fixation device 306, illustrated schematically in FIGS. 1 and 2, and as shown in the slice, or image 304, of FIG. 3, may be any conventional invasive, or noninvasive, fixation device which attaches to the patient 302 a coordinate system and secures the patient to the imaging table 301. Typically, the coordinate system is one which is forced by its attachment mechanism to be coplanar with the plane 307 in which lies the upper surface 308 of imaging table 301; however, any fixation device 306 having a coordinate system may be utilized provided the relationship between the coordinate system and the imaging table 301 is known, when it is desired to fixate patient 302.

Figure 3:
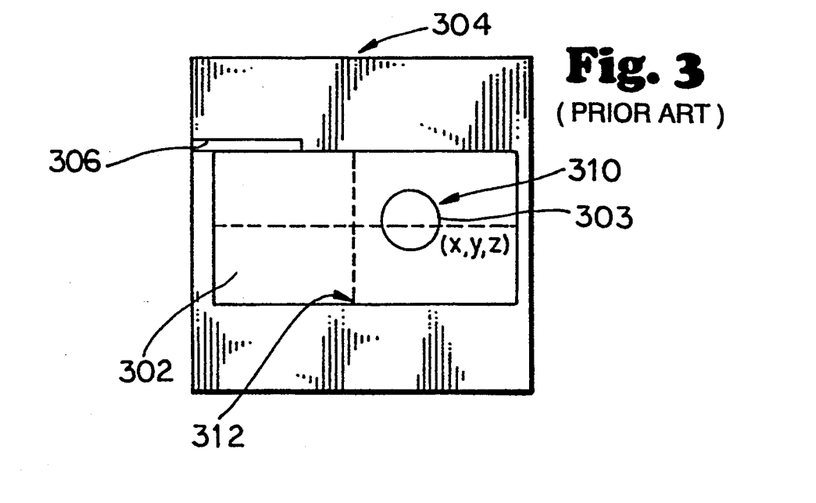
FIG. 3 is an example of an image produced by the imaging device of FIG. 1, illustrating the position of the lesion within the patient's body.

In FIG. 3, the lesion 303 is shown disposed within the patient's body 302 at a particular location having conventional X, Y, and Z coordinates, which are determined in a conventional manner by the CT scanner with respect to the frame of reference, or the coordinate system, of the imaging device as shown by its X, Y and Z axes in FIG. 1. It should be noted that the use of the term "lesion" throughout this specification, including the claims, is meant to include any lesion, tumor, abnormal growth, or similar structure, or body organ, which is desired to be treated with radiation therapy. The cross-sectional configuration of lesion 303 in FIG. 3 appears as circular, for illustrative purposes only.

Figure 9:
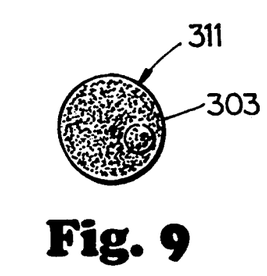
FIG. 9 is a three-dimensional rendering of the outline of the lesion of FIG. 6 prepared from a plurality of images like that of FIG. 3 obtained from the imaging device of FIG. 1.

After the series of slices, or images, 304 of the patient's body 302 which include lesion 303 therein, are obtained, the series of slices, or diagnostic images are then transferred in a conventional manner to a conventional radiation treatment planning system which includes conventional software to permit a physician to outline the outer surface 310 of lesion 303 in each slice 304. The computer software of the radiation treatment planning system also constructs, or creates, a three-dimensional rendering of the outer surface 310 of lesion 303 from the plurality of slices, or diagnostic images, 304. An example of a three-dimensional rendering 311 of the outline of a lesion 303 is shown in FIG. 9, and the three-dimensional rendering 311 is aligned with the frame of reference of the imaging device. In the case of imaging device 300 of FIG. 1, its frame of reference is the longitudinal axis 312, or Z axis, of imaging table 301. In a conventional manner, a radiation treatment plan is generated by the radiation treatment planning system, whereby lesion 303 may receive the necessary radiation dose to properly treat lesion 303. Preferably, the radiation treatment plan is a conformal radiation treatment plan, whereby the shape of the radiation beam will conform to the spacial contour, or outline, 310 of lesion 303 as seen by the radiation beam as it passes through the lesion 303, or the "beam's eye view" of the lesion 303 during rotation of the radiation beam source about the lesion 303.

Figure 4:
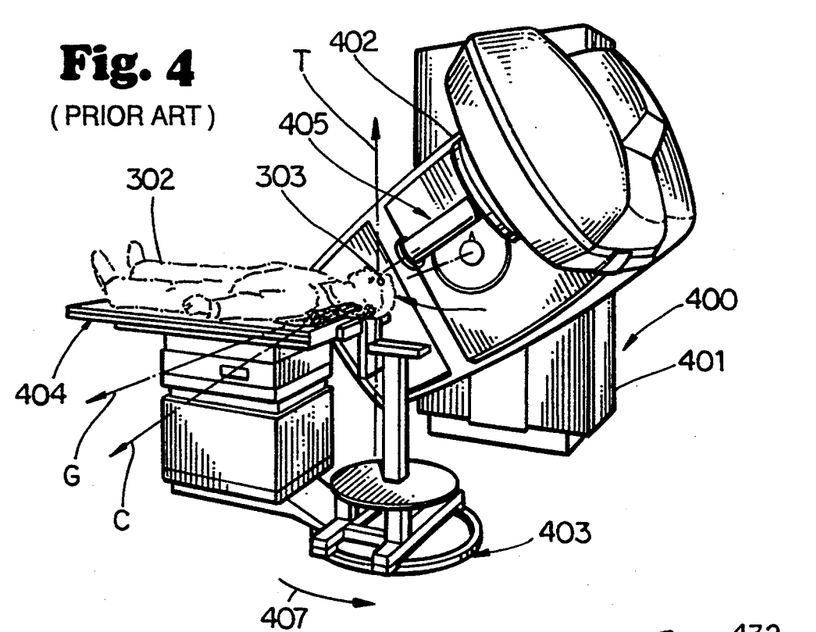
FIG. 4 is a perspective view of a conventional radiation therapy device, or linear accelerator, including a rotatable couch, collimator, and gantry.

With reference to FIG. 4, a conventional radiation treatment device 400, which is preferably a conventional linear accelerator 401, includes a gantry 402, turntable 403 which causes treatment table 404 to rotate therewith, and a collimator 405, which preferably is a collimator capable of conforming the shape of the radiation beam to conform to the beam's eye view of the lesion being treated. The three axes of rotation of the gantry 402, turntable and treatment table 403, 404 and collimator 405 are designated with the letters G, T, and C, respectively. For illustrative purposes only, the lesion 303 within patient's body 302 is disposed in the patient's head in FIG. 4; however, the method and apparatus of the present invention is limited to use with lesions disposed in the patient's body, or torso, excluding the head of the patient. The lesion 303 which is treated by linear accelerator 401 is disposed at the isocenter 406 of the linear accelerator 401. The isocenter 406 is defined as the point of intersection of the three axes of rotation, C, G, and T of linear accelerator 401. The previously described radiation treatment plan controls the operation of linear accelerator 401, and controls the operation of collimator 405, rotation of gantry 402, and location of treatment table 404, in a conventional manner. As previously discussed, the position and orientation of lesion 303 within patient's body 302 with respect to linear accelerator 401 may not necessarily be the same as the position and orientation of lesion 303 which was utilized in developing the radiation treatment plan. Thus, the present invention is used to verify that the position and orientation of lesion 303 within the patient's body 302 conforms, or matches, the position and orientation of the lesion 303 in the diagnostic slices 304 utilized in developing the radiation treatment plan.

Figure 5:
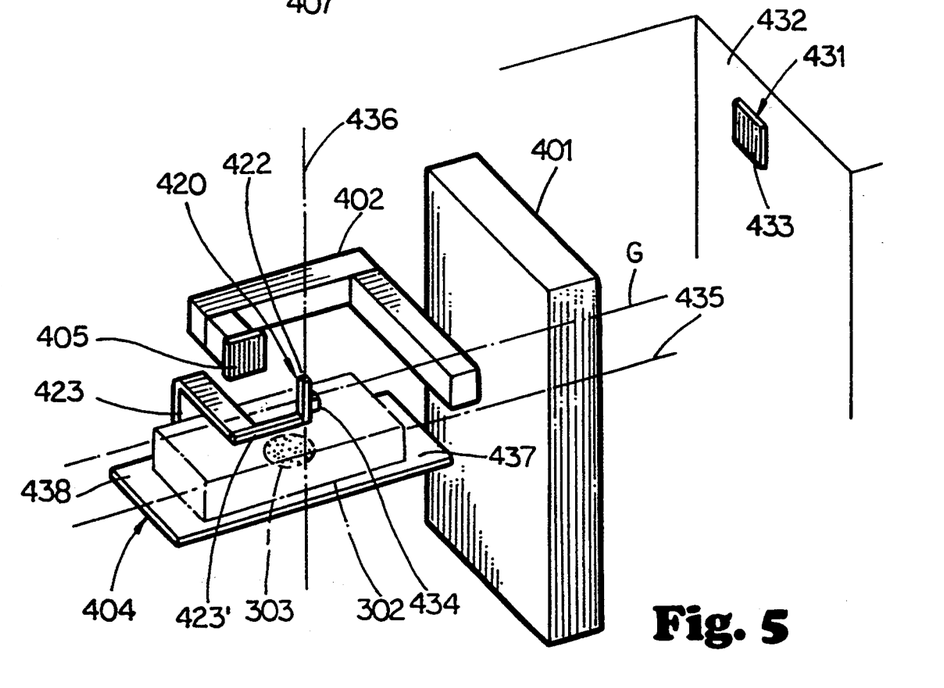
FIG. 5 is a perspective, schematic view, of the linear accelerator of FIG. 4, including a means for generating an ultrasound image of the lesion within the patient's body.

With reference to FIG. 5, the linear accelerator 401 of FIG. 4 is schematically illustrated, including treatment table 404, gantry 402, and collimator 405 illustrated with patient 302 lying upon treatment table 404. In FIG. 5, treatment table 404 has been rotated 90 degrees in the direction shown by arrow 407 of FIG. 4. Patient 302 is disposed on treatment table 404, with patient 302 laying flat upon treatment table 404, although patient 302 is not laying precisely in the same orientation with respect to treatment table 404, as patient 302 had when patient 302 was lying upon imaging table 301. Although it might be desirable to immobilize patient 302 during the radiation therapy treatment, due to the prolonged time required for many treatments, the patient's orientation on the treatment table 404 need Dot be precisely the same as its orientation on imaging table 301; however patient 302 must be laying flat on treatment table 404. Since the orientation of the patient's body 302 is not the same as it was when the patient 302 was imaged by imaging device 300, it should be apparent that it is very likely the position and orientation of lesion 303 with respect to treatment table 404 and linear accelerator 401 will not conform, or match, the position and orientation of lesion 303 upon which the radiation treatment plan for linear accelerator 401 has been based. It is thus necessary to verify the position, including the orientation, of lesion 303 to determine if it will conform to its desired position, including orientation, which has been used in the radiation treatment plan previously obtained. Further, it is necessary to determine where to relocate lesion 303 with respect to linear accelerator 401, so that the position and orientation of lesion 303 will conform to its position and orientation required by the radiation treatment plan.

The position, of lesion 303, which includes its orientation, may be verified in the following manner. A means for generating 420 an ultrasound image 421 (FIG. 7) is disposed on treatment table 404. Preferably the means for generating 420 an ultrasound image 421 is a conventional, commercially available ultrasound probe 422. Ultrasound probe 422 can generate two-dimensional ultrasound images of the portion of the patient's body 302 containing lesion 303, while patient 302 is on treatment table 404. Ultrasound probe 422 is disposed upon, and mounted to, treatment table 404 as by a bracket 423 which is preferably fixedly secured to treatment table 404. Ultrasound probe 422, by means of any suitable conventional connection 423' is mounted so that it can be moved upwardly and downwardly with respect to bracket 423, so that ultrasound probe 422 may be brought into contact with the patient's body 302, in order to generate ultrasound images 421.

Figure 6:
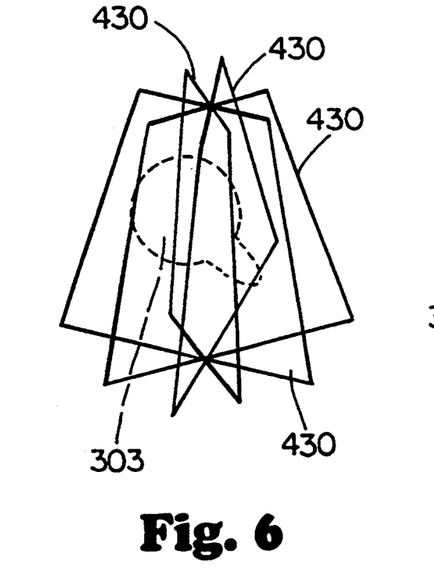
FIG. 6 is a perspective view indicating multiple ultrasound images being taken of a lesion.
Figure 7A:
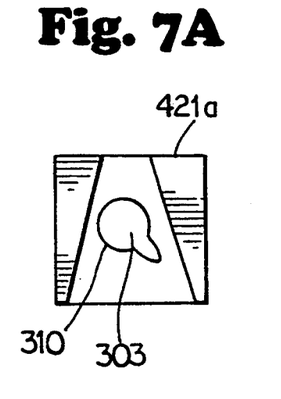
FIGS. 7A–7D are two-dimensional ultrasound images, with the lesion of FIG. 6 having its outer surface outlined.
Figure 7B:
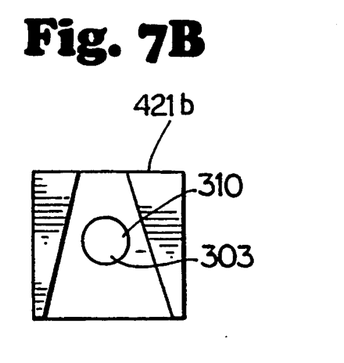
Figure 7C:
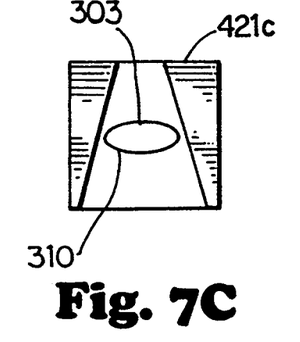
Figure 7D:
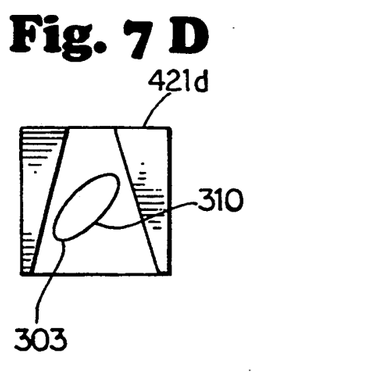

With reference to FIG. 6, lesion 303, shown in phantom lines, is shown disposed within a plurality of planes 430, each plane representing a particular orientation of ultrasound probe 422 while an ultrasound image 421 of lesion 303 is being generated. By rotating ultrasound probe 422, or alternatively by moving ultrasound probe 422 with respect to table 404, as will be hereinafter described in greater detail, the plurality of ultrasound images 421a–421d of FIGS. 7A–7D, may be generated. As seen in FIGS. 7A–7D, the outer surface of lesion 303 in each ultrasound image 421a–421d is outlined, such outlining being performed by a conventional software program, such as in the radiation treatment planning system previously described, which permits a physician to outline the outer surfaces 310 of each ultrasound image 421a–421d, in a similar manner in which the outer surface 310 of lesion 303 was outlined on the diagnostic images, or slices, 304. While only four ultrasound images are illustrated, this "is for illustrative purposes only, in that more ultrasound images 421 may be required dependent upon the size of lesion 303.

Figure 8:
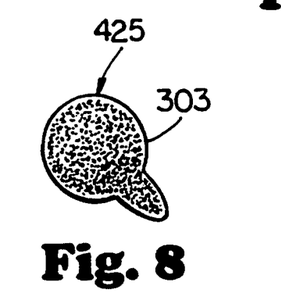
FIG. 8 is a three-dimensional rendering of the outline of a lesion prepared from the plurality of ultrasound images of FIG. 7.

As shown in FIG. 8, a three-dimensional rendering 425 of the outline of the lesion 303 from the plurality of two-dimensional ultrasound images 421a–421d may be formed by a conventional software program in a similar manner in which the three-dimensional rendering 311 of lesion 303 (FIG. 9) was prepared from the series of diagnostic images, or slices 304, as previously described.

In order to properly combine the ultrasound images 421a–421d, so that the three-dimensional renderings 425 and 311 of FIGS. 8 and 9 can be properly compared, as hereinafter described, it is necessary that the ultrasound probe 422 (FIG. 5) be disposed in a known geometric orientation. This geometric orientation for ultrasound probe 422 must be known for each ultrasound image 421a–421d which is generated by ultrasound probe 422. Preferably, the known geometric orientation is the orientation 9f the ultrasound probe 422 with respect to the coordinate system, or frame of reference, of the linear accelerator 401, which is along the longitudinal axis 435 of treatment table 404, which corresponds to the Z axis of the X, Y, and Z axes illustrated in FIG. 5.

Preferably, a means for indicating the geometric orientation of the ultrasound probe 422 is disposed within the room 432 in which linear accelerator 401 is installed.

The means for indicating 431 the geometric orientation of ultrasound probe 422, or means 431 for indicating the position of ultrasound probe 422 when each ultrasound image 421 is generated, is a position sensing system 433 aligned with linear accelerator 401. Any number of conventional position sensing systems can be used to determine the position of the ultrasound probe 422 with respect to the linear accelerator 401. These can include: a camera system fixed to the room 432 which looks at light emitting diodes ("LED") 434 mounted to ultrasound probe 422, which determines the orientation of the ultrasound probe 422 by the relationship between the positions of at least two LED's; ultrasonic emitters 434 affixed to the ultrasound probe 422 which are listened to by microphones placed in the room, whereby the position, or geometric orientation of ultrasound probe 422 is determined by triangulating the time it takes for the sound from each of the ultrasonic emitters, or transmitters, to reach a microphone disposed at a fixed location in the treatment room 432. Any suitable position sensing system 433 may be utilized, provided the position, including the orientation, of ultrasound probe 422 may be determined with respect to linear accelerator 401. With position sensing system 433, being aligned to the linear accelerator 401, then the position, and orientation of the ultrasound probe 422 with respect to the frame of reference of the linear accelerator 401 can be determined each time an ultrasound image 421 is generated. By mounting a portion of the position sensing system 433, such as LEDs or ultrasonic emitters shown schematically at 434, parallel to the longitudinal axis 436 of ultrasound probe 422, and by disposing ultrasound probe 422 to have its longitudinal axis 436 be disposed perpendicular to plane 437 in which lies the upper surface 438 of treatment table 404, the orientation of each ultrasound image 421a–421d with respect to the original diagnostic images 304 can be determined and compared. It should be noted, that the geometric orientation of ultrasound probe 422 with respect to linear accelerator 401, as previously described, is selected arbitrarily to provide the known geometric orientation for each ultrasound image 421 generated. However, it should be noted that by mounting the ultrasound probe 422 so that it is orthogonal, or perpendicular, to the frame of reference of both the linear accelerator 401 and imaging device 300, or longitudinal axis 435 of treatment table 404 and longitudinal axis 312 of imaging table 301, the comparison of the three-dimensional renderings 425, 311 of FIGS. 8 and 9 is simpler. The comparison of the three-dimensional renderings 425, 311 of FIGS. 8 and 9 can be accomplished so long as the position and orientation of ultrasound probe 422 is known when ultrasound probe 422 generates each ultrasound image 421a–421d.

Figure 10A:
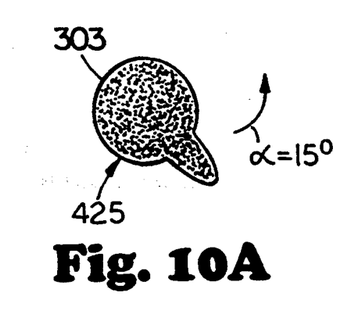
FIGS. 10A–10C illustrate the rotational transformation required for the three-dimensional rendering of FIG. 8 to be orientated into the same configuration of the lesion of FIG. 9.
Figure 10B:
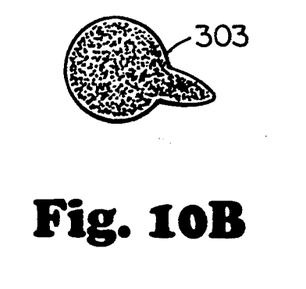
Figure 10C:
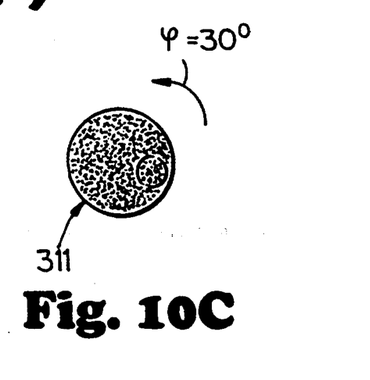

With reference to FIGS. 8, 9, and FIGS. 10A–10C, after the three-dimensional renderings 425, 311 have been formed as previously described, the three-dimensional rendering 425 formed from the plurality of ultrasound images 421a–421d (FIG. 7) are compared with the three-dimensional rendering 311 of the outline of the lesion 303 formed from the diagnostic images 304 of the radiation treatment plan. The three-dimensional renderings 425, 311 can be compared by overlaying the three-dimensional rendering 425 over the three-dimensional rendering 311. Since the frames of reference for the data sets with which the three-dimensional renderings 425, 311 are the same, those being the longitudinal axes 435, 312 of the linear accelerator 401 and the imaging device 300, a transformation matrix required to align the two three-dimensional renderings 425, 311 can be determined by a conventional computer program which utilizes a conventional fitting algorithm, known to those of ordinary skill in the art. Were the orientation of the two three-dimensional renderings to conform to each other, whereby three-dimensional rendering 425 conformed, or matched, three-dimensional rendering 311, then the position of the lesion 303 with respect to the radiation therapy device 400, or linear accelerator 401, would be verified to conform to the desired position of the lesion 303 which has been used in the radiation treatment plan, and the radiation treatment plan could begin. As illustrated in FIGS. 8 and 9, the position of the lesion 303 with respect to the linear accelerator 401 does not conform to the desired position of the lesion 303 in the radiation treatment plan. As shown in FIG. 10A, the fitting algorithm determines the required coordinate transformation, or transformation matrix, required to properly align the three-dimensional renderings of FIGS. 8 and 9. The fitting algorithm determines that it is necessary to rotate three-dimensional rendering 425 an angle $\alpha$ equal to $-15$ degrees, whereby lesion 303 will assume the position illustrated in FIG. 10B. The fitting algorithm then determines that lesion 303 of FIG. 10B must be rotated an angle $\phi$ equal to $-30$ degrees.

Figure 11:
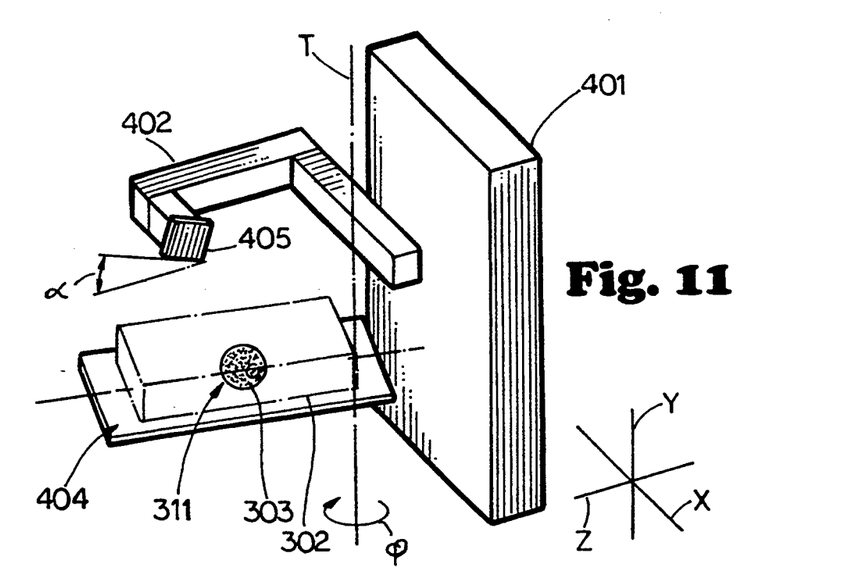
FIG. 11 is a perspective view of the radiation treatment device of FIG. 5, illustrating the lesion of FIG. 8 being orientated with respect to the radiation therapy treatment device, to conform to the orientation of the lesion of FIG. 9.

With reference to FIG. 11, the transformation matrix, or required coordinate transformation, is applied to linear accelerator 401, by rotating collimator 405 through the angle $\alpha$ $-15$ degrees, and treatment table 404 is rotated about its axis of rotation T through an angle $\phi$ of $-30$ degrees, whereby lesion 303 is positioned with respect to linear accelerator 401 so that lesion 303 conforms to its position and orientation it previously had when lesion 303 was imaged by imaging device 300 and the radiation treatment plan was developed. Accordingly, lesion 303 is oriented correctly with respect to linear accelerator 401 and is correctly positioned with respect to the isocenter 406 (FIG. 4) of the radiation beam from collimator 405. If desired, another plurality of ultrasound images may be generated for the lesion 303 in its position and orientation illustrated in FIG. 11, and by once again performing the steps discussed in connection with FIGS. 7-10 to confirm that lesion 303 is positioned and oriented in the desired position for the radiation treatment plan, prior to commencing the radiation treatment plan by linear accelerator 401 in a conventional manner.

The transformation matrix, or coordinate transformation, is determined by the fitting algorithm, which is the amount of movement of lesion 303 required to dispose lesion 303 with respect to linear accelerator 401 to conform to the desired position of lesion 303 in the radiation treatment plan. The desired amount of movement can be accomplished by: translating, or moving, linearly treatment table 404 upwardly, downwardly, or inwardly or outwardly from linear accelerator 401, such as along the X, Y, or Z axes illustrated in FIG. 11; rotating treatment table 404 about its axis of rotation T, as previously described in connection with FIG. 11; rotation of gantry 402 about its axis of rotation G; rotating collimator 405, as previously described in connection with FIG. 11; or any combination of the foregoing.

Figure 12:
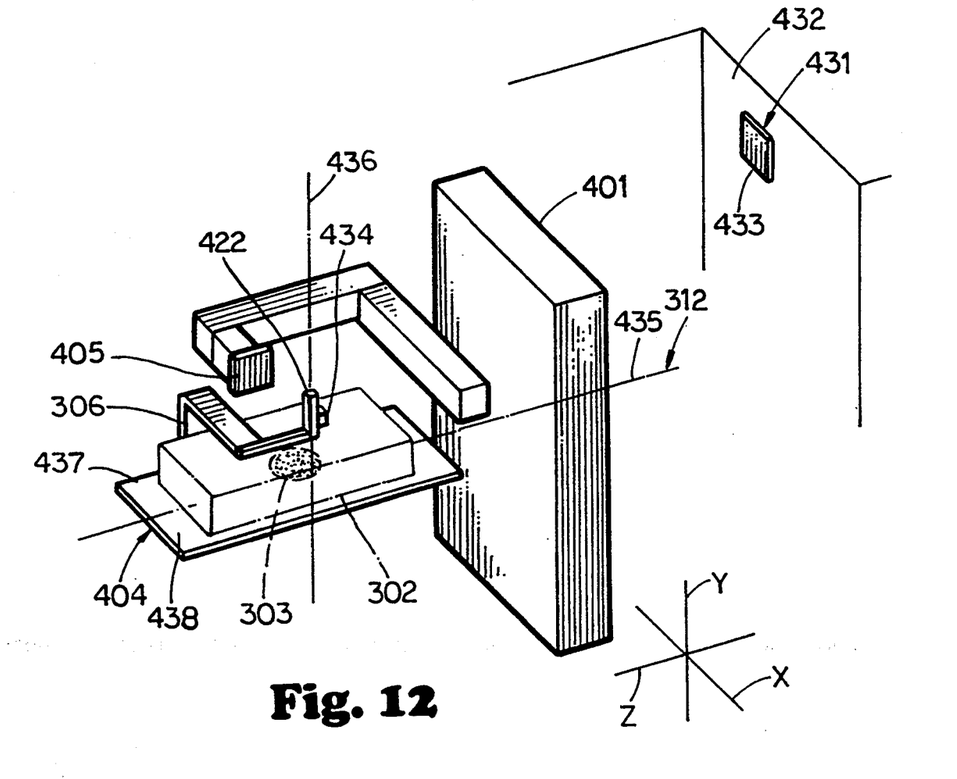
FIG. 12 is a perspective view of the radiation treatment device of FIG. 5, being provided with a patient fixation device to fixate the patient upon the treatment table of the radiation treatment device in the orientation the patient had when the patient was imaged with the imaging device of FIG. 1.

With reference to FIGS. 12-15, another method for verifying the position of lesion 303 will be described. The time required to perform the previously described method can be lessened if the patient 302 is fixated with respect to treatment table 404 in the same orientation that patient 302 was oriented when the patient was imaged as previously described in connection with FIGS. 1-3. If the patient 302 is fixated to imaging table 301, as by fixation device 306 previously described in connection with FIGS. 1-3, and if patient 302 is fixated to treatment table 404, as by use of the same fixation device 306, as shown in FIG. 12, it is only necessary to compare two-dimensional outlines of the outer surface 310 of lesion 303 obtained from at least one, and preferably only one, ultrasound image 421 with two-dimensional outlines of the outer surface of lesion 303 obtained from at least one diagnostic image, or slice 304. In this method of lesion position verification, patient 302 is imaged in imaging device 300 while the patient is fixated to imaging table 301 by fixation device 306 in the same manner as previously described in connection with FIGS. 1-3. The physician then outlines the outer surface 310 of lesion 303 in each of the diagnostic images, or slices, 304 in the same manner previously described in connection with FIG. 3. A radiation treatment plan is then developed for treatment of lesion 303 by a treatment planning system in the same manner previously described. The treatment planning system may also determine the center of a geometric solid, such as a sphere, cube, or other geometric solid, as is known in the art, which bounds the three-dimensional rendering 311 (FIG. 9) of the outer surface 310 of lesion 303, which information may be used in a manner hereinafter described.

With reference to FIG. 12, patient 302 is then disposed on treatment table 404 in the same orientation patient 302 was disposed upon imaging table 301. This may be accomplished by utilizing the same fixation device 306 on imaging table 404, whereby it is assured that patient 302 is referenced with respect to the two table 404,301 in an identical orientation. Once again, the patient 302 is laying flat upon treatment table 404. Table 404 is then moved with respect to linear accelerator 401 to dispose lesion 303 with respect to linear accelerator 401 in a position previously determined by the radiation treatment plan of the treatment planning system. By moving treatment table 404 along its X, Y, Z axes to the previously determined three-dimensional coordinates determined by the radiation treatment plan, lesion 303 will be disposed properly under the treatment beam from collimator 405.

Ultrasound probe 422 is then secured to treatment table 404 in a known geometric orientation, as by securing it to fixation device 306 which also functions in the same manner as bracket 423, previously described in connection with FIG. 5. At least one, and preferably only one, two-dimensional ultrasound image 421, (FIGS. 13, 14) is then generated by ultrasound probe 422, with the ultrasound probe 422 being disposed in a known geometric orientation for each ultrasound image generated. A position sensing system 433, as previously described in connection with FIG. 5 may be utilized to determine the orientation and position of ultrasound probe 422 in the manner previously described in connection with FIG. 5. As previously described in connection with FIG. 5, ultrasound probe 422 may be disposed with its longitudinal axis 436 being disposed perpendicular to the longitudinal axis 312 of treatment table 404, and perpendicular to the plane 437 in which lies the upper surface 438 of treatment table 404. Ultrasound probe 422 is moved downwardly to contact the patient 302 directly over the position of lesion 303 which the treatment planning system has determined for the location of lesion 303. Ultrasound probe 422 may then be moved with respect to lesion 303 a known distance along the longitudinal axis 435 of treatment table 404 and another ultrasound image is generated, if desired. Ultrasound probe 422 may be moved with respect to lesion 303, as by indexing fixation device 306 in a direction along the longitudinal axis 435 of treatment table 404. Ultrasound probe 422 is moved along axis 435 and ultrasound images are generated of lesion 303, until the entire length of lesion 303 along axis 435 has been imaged, if desired.

The outer surface 310 of lesion 303 of the at least one ultrasound image is then outlined in the manner previously described in connection with FIG. 7. The center of the geometric solid which bounds the three-dimensional rendering 425 (FIG. 8) of lesion 303 may also be determined in the same manner as the three-dimensional coordinates of the center of the geometric solid which bounds the three-dimensional rendering 311 (FIG. 9) of lesion 303.

The outline of the outer surface 310 of the lesion 303 of the at least one ultrasound image 421 is then compared with the outlines of the outer surface 310 of the lesion 303 of the corresponding diagnostic image, or slice, 304. If the lesion 303 has not moved from its position at the time of the imaging procedure, the outline of the ultrasound image and the diagnostic image should closely coincide. If the position of lesion 303 has moved since the time of the imaging procedure, then the amount of movement of lesion 303 along each of the X, Y, and Z axes of treatment table 404 can be determined by the previously described fitting algorithm to determine the required coordinate transformation for lesion 303, or treatment table 404 along the X, Y, and Z axes of FIG. 12. Alternatively, the three-dimensional coordinates of the centers of the geometric solids previously determined can be compared to determine the amount of movement of lesion 303 along the X, Y, and Z axes of FIG. 12 with respect to linear accelerator 401 which is necessary to conform the position of lesion 303 to the desired position of lesion 303 required by the radiation treatment plan.

Figure 13:
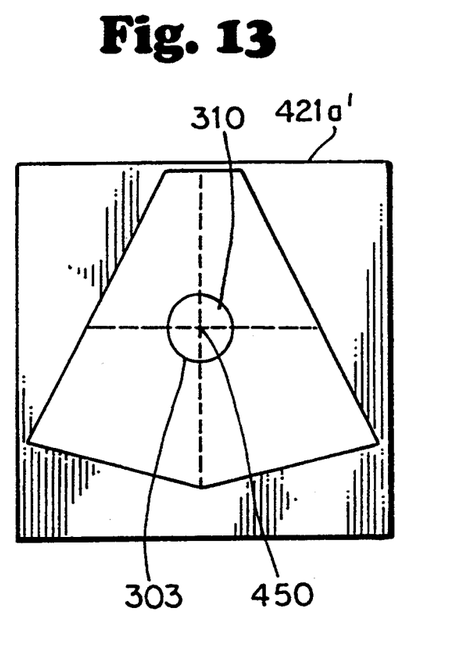
FIG. 13 is a two-dimensional ultrasound image made with the device of FIG. 12.
Figure 14:
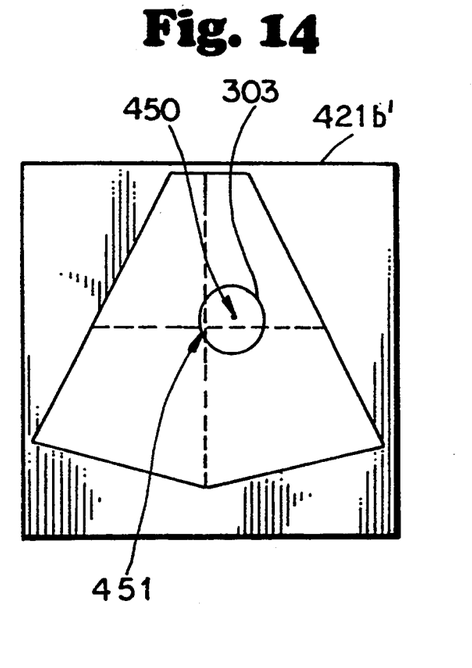
FIG. 14 is another two-dimensional ultrasound image made with the device of FIG. 12.

FIG. 13 illustrates an ultrasound image 421a' wherein the outline of the outer surface 310 of lesion 303 is properly disposed with respect to linear accelerator 401, whereby the center 450 of lesion 303 for that particular ultrasound image corresponds to the center of the diagnostic image or the diagnostic image taken at the same location along the longitudinal axis 312 of imaging device 300. FIG. 14 illustrates an ultrasound image 421b' of lesion 303, wherein the center 450 of lesion 303 has moved with respect to the desired center 451 of lesion 303 for the same corresponding location along axis 312 of imaging device 300.

Figure 15:
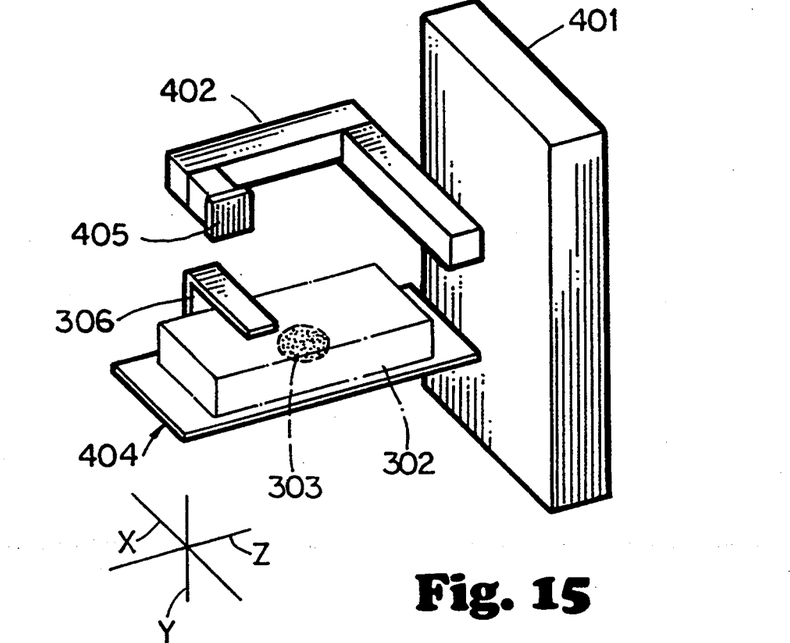
FIG. 15 is a perspective view of the radiation therapy device of FIG. 12, with the treatment table being reorientated so that the lesion within the patient's body conforms to the position of the lesion in a radiation treatment plan.

With reference to FIG. 15, the treatment table 404 has been moved along the X, Y, and Z axes of linear accelerator 401 and treatment table 404 to conform the position of lesion 303 to the desired position of lesion 303 of the radiation treatment plan. Ultrasound probe 422 has been removed so that the radiation therapy treatment may be delivered. If desired, another ultrasound study, as previously described, may be made for lesion 303 to confirm that lesion 303 is disposed in the proper position as required by the radiation treatment plan, before the radiation therapy is delivered.

It is to be understood that the invention is not to be limited to the exact details of construction, operation, exact materials or embodiment shown and described, as obvious modifications and equivalents will be apparent to one skilled in the art. Accordingly, the invention is therefore to be limited only by the scope of the appended claims.

I claim:

1. A lesion position verification system for use in a radiation therapy plan, for use with a radiation therapy device, for treating a lesion within a body of a patient, comprising:
   (a) a means for generating at least one ultrasound image of the lesion in the patient's body; and
   (b) a means for indicating the position, with respect to the radiation therapy device, of the means for generating the at least one ultrasound image when the ultrasound image is generated, whereby the position of the lesion in the ultrasound image can be compared with a position of the lesion in the radiation therapy plan.

2. The lesion position verification system of claim 1, wherein the means for generating the ultrasound image is an ultrasound probe.

3. The lesion position verification system of claim 2, including a means for mounting the ultrasound probe to the radiation therapy device.

4. The lesion position verification system of claim 1, wherein the means for indicating the position of the means for generating the at least one ultrasound image, is a position sensing system which indicates the position of the ultrasound image generating means with respect to the radiation therapy device.

5. The lesion position verification system of claim 1, further including a means for comparing the position of the lesion in the at least one ultrasound image with the position of the lesion in the radiation therapy plan.

6. A method for verifying the position of a lesion, having an outer surface, within a body of a patient for use in a radiation treatment plan which includes a plurality of diagnostic images, which each depict an outline of the outer surface of the lesion, comprising the steps of:
   (a) disposing the patient on a treatment table of a radiation therapy device;
   (b) disposing on the treatment table a means for generating an ultrasound image;
   (c) generating at least one two-dimensional ultrasound image of the lesion in the patient's body, with the ultrasound image generating means being disposed in a known geometric orientation for each ultrasound image generated;
   (d) outlining the outer surface of the lesion in at least one of said ultrasound images; and
   (e) comparing the outlines of the outer surface of the lesion of the said at least one ultrasound image with the outline of the outer surface of the lesion of at least one of the diagnostic images, whereby the position of the lesion with respect to the radiation therapy device may be verified to conform to a desired position of the lesion in the radiation treatment plan.

7. The method of claim 6, including the step of: determining an amount of movement of the lesion required to dispose the lesion, with respect to the radiation therapy device, to conform to the desired position of the lesion in the radiation treatment plan.

8. The method of claim 7, including the step of moving the lesion with respect to the radiation therapy device to dispose the lesion to conform to the desired position of the lesion in the radiation treatment plan.

9. The method of claim 8, including repeating steps (b) through (e) of claim 6.

10. The method of claim 8, wherein the step of moving the lesion is performed by moving the treatment table with respect to the radiation therapy device.

11. The method of claim 8, wherein the step of moving the lesion is performed by rotating the treatment table with respect to the radiation therapy device.

12. The method of claim 8, wherein the step of moving the lesion is performed by rotating a collimator of the radiation therapy device.

13. The method of claim 8, wherein the step of moving the lesion is performed by rotating a gantry of the radiation therapy device.

14. The method of claim 6, wherein the patient is disposed on the treatment table with the patient lying flat on the treatment table.

15. The method of claim 6, including the step of utilizing a means for indicating the geometric orientation of the ultrasound image generating means while the at least one ultrasound image is generated.

16. The method of claim 6, including the steps of: forming a three dimensional rendering of the outline of the lesion from a plurality of two-dimensional ultrasound images which have had the outer surface of the lesion outlined; and comparing the three dimensional rendering of the outline of the lesion of the ultrasound images with a three-dimensional rendering of the outline of the lesion of the radiation treatment plan.

17. The method of claim 6, including the step of disposing the patient on the treatment table by fixating the patient to the table with a patient fixation device in a known orientation.

18. The method of claim 17, including the step of determining a set of three dimensional coordinates of a center of a geometric solid which bounds the outer surface of the lesion in the at least one ultrasound image.

19. The method of claim 18, including the step of comparing the set of three-dimensional coordinates of the center of the geometric solid from the at least one ultrasound image to a set of three dimensional coordinates of a center of the same geometric solid determined from the diagnostic images.

20. The method of claim 17, wherein the ultrasound image generating means is disposed on the treatment table by mounting the ultrasound image generating means perpendicular to the treatment table.

* * * * *